United States Patent [19]

Aoki

[11] 4,327,079

[45] Apr. 27, 1982

[54] DENTIFRICE COMPOSITIONS

[75] Inventor: Hideki Aoki, Funabashi, Japan

[73] Assignee: Dental Chemical Co., Ltd., Tokyo, Japan

[21] Appl. No.: 201,727

[22] Filed: Oct. 29, 1980

[30] Foreign Application Priority Data

Nov. 15, 1979 [JP] Japan .............................. 54/147011

[51] Int. Cl.$^3$ .............................................. A61K 9/16
[52] U.S. Cl. .................................... 424/57; 424/49
[58] Field of Search ................................ 424/49–58, 424/128

[56] References Cited

U.S. PATENT DOCUMENTS

| | | | |
|---|---|---|---|
| 1,817,664 | 8/1931 | Badanes | 424/49 |
| 2,658,851 | 11/1953 | Brandenberger et al. | 424/49 |
| 2,994,642 | 8/1961 | Bossard | 424/49 |
| 3,679,360 | 7/1972 | Rubin et al. | 424/128 |
| 3,689,636 | 9/1972 | Svajda | 424/49 |
| 3,691,272 | 9/1972 | Asche | 424/57 |
| 4,048,300 | 9/1977 | Tomlinson et al. | 424/52 |
| 4,080,440 | 3/1978 | DiGiulio et al. | 424/49 |
| 4,083,955 | 4/1978 | Grabenstetter et al. | 424/49 |
| 4,108,980 | 8/1978 | Duff | 424/52 |

*Primary Examiner*—Shep K. Rose
*Attorney, Agent, or Firm*—Paul & Paul

[57] ABSTRACT

A dentifrice composition containing synthetic hydroxyapatite powder which is neutral or weakly alkaline or contains 0.1 to 20% by weight of NaCl and/or KCl and 0.003 to 3% by weight of $MgCl_2$. The dentifrice composition is very effective in fortifying a surface of a tooth, promoting remineralization of the surface of the tooth and eliminating plaque from the tooth.

1 Claim, No Drawings

DENTIFRICE COMPOSITIONS

The invention relates to dentifrice compositions.

According to the present invention, there is provided a dentifrice composition containing synthetic hydroxyapatite powder and being neutral or weakly alkaline.

It has been found that the dentifrice composition of the present invention is very effective in fortifying a surface of a tooth, promoting remineralization of the surface of the tooth and eliminating plaque (a colony of bacteria).

In general, a conventional dentifrice contains, as a tooth-cleaning and abrading agent, a mineral, such as colloidal silica, calcium phosphate, calcium carbonate, magnesium carbonate, etc. While these abrading agents are used to remove contaminants on teeth, it is essential that they do not harm the teeth.

Since the dentifrice composition of the present invention contains a suitable amount of synthetic hydroxyapatite powder, plaque as well as substances contaminating teeth can be removed very effectively. We presume this is due to the fact that the synthetic hydroxyapatite has a hardness similar to that of the enamel portion of the tooth and it can impart an appropriate abrading effect on the enamel portion of the tooth in brushing the teeth. We further presume this is also due to the fact that the synthetic hydroxyapatite has a large surface area and an excellent absorptivity. We have further found that the synthetic hydroxyapatite powder has the effect of strengthening the coating on and remineralization the surface of the enamel of the tooth.

In accordance with the present invention, there is further provided a dentifrice composition containing synthetic hydroxyapatite powder and, based on the weight of the composition, 0.1 to 20% by weight of NaCl and/or KCl and 0.003 to 3% by weight of $MgCl_2$.

It has also been found that the presence of a mixture of NaCl and/or KCl with $MgCl_2$ in a dentifrice composition containing synthetic hydroxyapatite powder can effectively promote the elimination of plaque from teeth and the fortification and remineralization of the surfaces of the teeth.

More specifically, the latter dentifrice composition of the present invention can effectively deposit and coat crystals of hydroxyapatite on the surfaces of the teeth. We presume this is due to the fact that the solubility of hydroxyapatite in water is increased in the presence of the chlorides as specified above. More particularly, since hydroxyapatite is a salt which only slightly soluble in water, the ion products of ions such as $[Ca^{++}]$, $[HPO_4^{--}]$, etc. ionized in the dentifrice are small. This means that the ion products for promoting coating on the surfaces of the teeth, i.e. deposition of the crystals of hydroxyapatite on the surfaces of the teeth are small. However, if NaCl and/or KCl and $MgCl_2$ are added to the dentifrice containing hydroxyapatite, it is presumed that the solubilities of $Ca^{++}$ and $HPO_4^{--}$ are increased very much and the coating on the teeth is enhanced.

In cases where the amounts of NaCl and/or KCl and $MgCl_2$ contained in the dentifrice composition of the present invention are smaller than those specified above, a sufficient coating effect cannot be obtained, while in cases where such amounts are larger than those specified above, it becomes difficult to give a comfortable feeling in the use of the dentifrice composition.

To obtain a suitable abrading effect and desired plaque elimination, the average particle size of the hydroxyapatite powder is preferably about $2\mu$ and the maximum particle size thereof is preferably $10\mu$ or less.

The dentifrice composition of the present invention may include various additives which are commonly employed in dentifrices and may further include, if desired, citric acid, lactic acid, acetic acid, pyrrolic acid, glutamine, proline, serine, glycine, etc.

The invention will be further illustrated with reference to the following examples. Examples 1 to 7 and 11 to 17 respectively show formulations of the dentifrice compositions in accordance with the present invention in terms of parts by weight and Examples 8 to 10, 18 and 19 are to substantiate effects of the composition of the present invention.

EXAMPLE 1

| Tooth Paste | |
|---|---|
| Apatite Powder | 13.2 |
| Calcium phosphate | 25.0 |
| CMC sodium salt | 0.3 |
| Carrageenan | 1.2 |
| Glycerin | 10.0 |
| Solbitol | 15.0 |
| Sodium lauryl sulfate | 2.0 |
| Flavor | 1.2 |
| Sodium saccharinate | 0.1 |
| Silicon dioxide | 2.0 |
| Water | 30.0 |

EXAMPLE 2

| Tooth Paste | |
|---|---|
| Apatite powder | 7.2 |
| Calcium phosphate | 10.0 |
| Calcium pyrophosphate | 20.0 |
| CMC Sodium salt | 1.0 |
| Sodium alginate | 0.1 |
| Glycerin | 10.0 |
| Solbitol | 10.0 |
| Sodium lauryl sulfate | 1.5 |
| Sodium lauryl sarcosinate | 0.5 |
| Flavor | 0.5 |
| Sodium saccharinate | 0.1 |
| Silicon dioxide | 2.5 |
| Sodium phosphate | 1.0 |
| Water | 35.0 |

EXAMPLE 3

| Tooth Paste | |
|---|---|
| Apatite powder | 22.3 |
| Calcium pyrophosphate | 10.0 |
| CMC sodium salt | 0.5 |
| Carrageenan | 0.6 |
| Glycerin | 20.0 |
| Solbitol | 10.0 |
| Sodium lauryl sulfate | 2.0 |
| Flavor | 1.0 |
| Sodium saccharinate | 0.1 |
| Silicon dioxide | 2.0 |
| Sodium phosphate | 0.5 |
| Water | 30.0 |

EXAMPLE 4

| Tooth Paste | |
|---|---|
| Apatite powder | 38.1 |
| CMC sodium salt | 1.0 |
| Carrageenan | 0.3 |
| Glycerin | 35.0 |
| Sodium lauryl sulfate | 2.0 |
| Flavor | 1.0 |
| Sodium saccharinate | 0.1 |
| Silicon dioxide | 2.5 |
| Water | 20.0 |

EXAMPLE 5

| Tooth Powder | |
|---|---|
| Apatite powder | 96.3 |
| Sodium lauryl sulfate | 2.0 |
| Flavor | 1.5 |
| Sodium saccharinate | 0.2 |

EXAMPLE 6

| Tooth Powder | |
|---|---|
| Apatite powder | 40.7 |
| Calcium pyrophosphate | 50.0 |
| Silicon dioxide | 5.0 |
| Sodium lauryl sulfate | 2.0 |
| Flavor | 2.0 |
| Sodium saccharinate | 0.3 |

EXAMPLE 7

| Wet Tooth Powder | |
|---|---|
| Apatite powder | 65.38 |
| Calcium phosphate | 10.0 |
| Solbitol | 10.0 |
| Sodium lauryl sulfate | 2.0 |
| Flavor | 1.5 |
| Calcium phosphate | 1.0 |
| Water | 10.0 |
| Sodium saccharinate | 0.12 |

EXAMPLE 8

0.1% solution of Neutral Red was applied to the front teeth of each of three male adults A, B and C (22 to 25 years old), who had been using conventional commercially available dentifrices. Thereafter, similar dyeing operation was conducted one day after they started to use the dentifrice of Example 1 and the plaque-stained areas before and after the change of the dentifrices were compared. In the case of A, the stained area after the change was about 10% of the initial stained area and it was confirmed that the decontamination of the plaque area was about 90%. In cases of B and C, the decontamination of the plaque areas was about 50%.

EXAMPLE 9

Abrasive effects of dentifrices were tested using, for teeth, plate-form bodies made of sintered hydroxyapatite having a hardness similar to that of an enamel portion of a tooth. The plate-form bodies were each subjected to brushing using tooth brushes and different dentifrices for 60 minutes. The losses in weights of the respective plate-form bodies were measured. In the result, the abrasive effects of the dentrifrice composition of the present invention was similar to those of commercially available dentifrices (WHITE & WHITE and DENTER LION).

EXAMPLE 10

An adult's permanent tooth was sliced in two using a prisma adamantinum to form a section having a thickness of about 200 μm. A supernant saturated solution of a liquid prepared by stirring 1 g of hydroxyapatite powder with 100 ml of distilled water was passed over the thus formed section at a flow rate of 0.6 ml/min. The section was observed continuously using a polarization microscope and it was confirmed that the section was coated with analogous apatite crystals about 1 μm thick after 14 hours.

EXAMPLE 11

| Tooth Paste | |
|---|---|
| Apatite powder | 10.0 |
| Calcium phosphate | 25.0 |
| CMC sodium salt | 0.3 |
| Carrageenan | 1.2 |
| Glycerin | 10.0 |
| Solbitol | 15.0 |
| Sodium lauryl sulfate | 2.0 |
| Flavor | 1.2 |
| Sodium saccharinate | 0.1 |
| Silicon dioxide | 2.0 |
| NaCl | 0.27 |
| $MgCl_2$ | 0.01 |
| Water | 32.92 |

EXAMPLE 12

| Tooth Paste | |
|---|---|
| Apatite powder | 5.0 |
| Calcium phosphate | 10.0 |
| Calcium pyrophosphate | 20.0 |
| CMC sodium salt | 1.0 |
| Sodium alginate | 0.1 |
| Glycerin | 10.0 |
| Solbitol | 10.0 |
| Sodium lauryl sulfate | 1.5 |
| Sodium lauryl sarcosinate | 0.5 |
| Flavor | 0.5 |
| Sodium saccharinate | 0.1 |
| Silicon dioxide | 2.5 |
| NaCl | 3.0 |
| $MgCl_2$ | 0.2 |
| Water | 35.0 |

EXAMPLE 13

| Tooth Paste | |
|---|---|
| Apatite powder | 20.0 |
| Calcium pyrophosphate | 10.0 |
| CMC sodium salt | 0.5 |
| Carrageenan | 0.6 |
| Glycerin | 20.0 |
| Solbitol | 10.0 |
| Sodium lauryl sulfate | 2.0 |
| Flavor | 1.0 |
| Sodium saccharinate | 0.1 |
| Silicon dioxide | 2.0 |
| KCl | 2.0 |
| $MgCl_2$ | 0.3 |
| Sodium phosphate | 0.5 |

EXAMPLE 14

| Tooth Paste | |
| --- | --- |
| Apatite powder | 35.0 |
| CMC sodium salt | 1.0 |
| Carrageenan | 0.3 |
| Glycerin | 35.0 |
| Sodium lauryl sulfate | 2.0 |
| Flavor | 1.0 |
| Sodium saccharinate | 0.1 |
| Silicon dioxide | 2.5 |
| NaCl | 2.0 |
| $MgCl_2$ | 0.1 |
| KCl | 1.0 |
| Water | 20.0 |

-continued

| Tooth Paste | |
| --- | --- |
| Water | 30.0 |

EXAMPLE 15

| Tooth Powder | |
| --- | --- |
| Apatite powder | 90.8 |
| Sodium lauryl sulfate | 2.0 |
| Flavor | 1.5 |
| Sodium saccharinate | 0.2 |
| NaCl | 5.0 |
| $MgCl_2$ | 0.5 |

EXAMPLE 16

| Tooth Powder | |
| --- | --- |
| Apatite powder | 38.0 |
| Calcium pyrophosphate | 50.0 |
| Silicon dioxide | 5.0 |
| Sodium lauryl sulfate | 2.0 |
| Flavor | 2.0 |
| Sodium saccharinate | 0.3 |
| NaCl | 1.8 |
| $MgCl_2$ | 0.2 |
| Potassium phosphate | 0.7 |

EXAMPLE 17

| Wet Tooth Powder | |
| --- | --- |
| Apatite powder | 63.0 |
| Calcium phosphate | 10.0 |
| Solbitol | 10.0 |
| Sodium lauryl sulfate | 2.0 |
| Flavor | 1.5 |
| NaCl | 3.3 |
| $MgCl_2$ | 0.08 |
| Water | 10.0 |
| Sodium saccharinate | 0.12 |

EXAMPLE 18

1 g of hydroxyapatite powder was introduced into 100 ml of 37° C. distilled water and NaCl and $MgCl_2$ were added in various concentrations. The calcium ion concentrations of the respective solutions were measured and it was confirmed that the solubility of hydroxyapatite was increased by adding NaCl and $MgCl_2$. The calcium ion concentrations 10 days after the preparation of the solutions were as follows:

| NaCl concentration; | 0 | 0.3 | 0.3 | 3.0 | 3.0 | (%) |
| --- | --- | --- | --- | --- | --- | --- |
| $MgCl_2$ concentration; | 0 | 0.03 | 0.3 | 0.03 | 0.3 | (%) |
| $Ca^{++}$ concentration; | 4.9 | 26.0 | 31.2 | 31.5 | 36.7 | (ppm) |

EXAMPLE 19

An adult's permanent tooth was sliced in two using a prisma adamantinum to prepare a section about 200 μm thick. The enamel portion was removed to expose the dentin portion. A hydroxyapatite-saturated solution in distilled water containing 0.001% of $MgCl_2$ and 0.9% of NaCl was passed over the so prepared section at a flow rate of 0.6 ml/min. The section was continuously observed using a polarization microscope and it was confirmed that all over the surfaces of the section were coated with analogous apatite crystals at a thickness of about 5 μm.

I claim:

1. A dentifrice composition for tooth paste consisting essentially of: 30 to 35 parts by weight of an abrading agent containing 5 to 35 parts by weight of synthetic hydroxyapatite powder and the balance of at least one member selected from the group consisting of calcium phosphate and calcium pyrophosphate; 20 to 35 parts by weight of at least one filler selected from the group consisting of glycerin and sorbitol; 30 to 35 parts by weight of water; 0.27 to 3 parts by weight of at least one alkali metal chloride selected from the group consisting of NaCl and KCl; and, 0.01 to 0.3 parts by weight of $MgCl_2$.

* * * * *